(12) United States Patent
Leeton

(10) Patent No.: US 10,584,079 B2
(45) Date of Patent: Mar. 10, 2020

(54) MODIFIED HF ALKYLATION REACTION ZONE FOR IONIC LIQUID ALKYLATION

(71) Applicant: UOP LLC, Des Plaines, IL (US)

(72) Inventor: Eric Leeton, Corpus Christi, TX (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/877,988

(22) Filed: Jan. 23, 2018

(65) Prior Publication Data

US 2018/0148393 A1    May 31, 2018

Related U.S. Application Data

(63) Continuation of application No. PCT/US2016/042888, filed on Jul. 19, 2016.
(Continued)

(51) Int. Cl.
*C07C 2/58* (2006.01)
*C07C 2/56* (2006.01)
(Continued)

(52) U.S. Cl.
CPC .............. *C07C 2/58* (2013.01); *B01J 31/02* (2013.01); *B01J 31/0277* (2013.01); *B01J 35/12* (2013.01); *C07C 2/60* (2013.01); *C10G 29/205* (2013.01); *C10L 1/06* (2013.01); *C07C 2531/02* (2013.01); *C10L 2270/023* (2013.01); *C10L 2290/24* (2013.01); *C10L 2290/54* (2013.01); *C10L 2290/543* (2013.01)

(58) Field of Classification Search
CPC ... C10G 2/58; C10G 2/60; C10G 2/62; C10G 2531/02; C10G 2531/14; C07C 2/58; C07C 2/60; C07C 2/62; C07C 2531/02; C07C 2531/14
See application file for complete search history.

(56) References Cited

U.S. PATENT DOCUMENTS

| | | |
|---|---|---|
| 5,098,668 A | 3/1992 | Callen et al. |
| 5,707,923 A | 1/1998 | Hutchens et al. |
| | (Continued) | |

FOREIGN PATENT DOCUMENTS

| | | |
|---|---|---|
| CN | 101365664 A | 2/2009 |
| CN | 101910368 A | 12/2010 |
| | (Continued) | |

OTHER PUBLICATIONS

Search Report dated Nov. 3, 2016 for corresponding PCT Appl. No. PCT/US2016/042888.
(Continued)

*Primary Examiner* — Youngsul Jeong

(57) ABSTRACT

An alkylation process and apparatus are described. The alkylation process includes pre-mixing a paraffin stream with an ionic liquid catalyst stream from a settler. The premixed paraffin and ionic liquid catalyst stream is mixed in a low-efficiency pump to form a paraffin and ionic liquid catalyst mixture. An olefin feed stream is introduced into a riser reactor. The paraffin and ionic liquid catalyst mixture is introduced into the riser reactor to form a reaction mixture comprising alkylate and the ionic liquid catalyst. The reaction mixture is separated in a settler into an ionic liquid catalyst stream and a hydrocarbon stream.

17 Claims, 2 Drawing Sheets

Related U.S. Application Data

(60) Provisional application No. 62/196,171, filed on Jul. 23, 2015.

(51) Int. Cl.
*C07C 2/60* (2006.01)
*B01J 31/02* (2006.01)
*C10G 29/20* (2006.01)
*C10L 1/06* (2006.01)
*B01J 35/12* (2006.01)

(56) References Cited

U.S. PATENT DOCUMENTS

| | | | |
|---|---|---|---|
| 7,651,970 | B2 | 1/2010 | Elomari et al. |
| 7,674,739 | B2 | 3/2010 | Elomari et al. |
| 7,674,740 | B2 | 3/2010 | Harris et al. |
| 7,678,727 | B2 | 3/2010 | Harris et al. |
| 7,691,771 | B2 | 4/2010 | Harris et al. |
| 7,727,925 | B2 | 6/2010 | Elomari et al. |
| 7,732,363 | B2 | 6/2010 | Elomari et al. |
| 7,737,067 | B2 | 6/2010 | Elomari et al. |
| 7,825,055 | B2 | 11/2010 | Elomari et al. |
| 7,956,002 | B2 | 6/2011 | Elomari et al. |
| 8,183,425 | B2 * | 5/2012 | Luo ................ C07C 2/60 585/714 |
| 8,227,366 | B2 | 7/2012 | Mehlberg |
| 8,524,623 | B2 | 9/2013 | Timken et al. |
| 8,524,965 | B2 * | 9/2013 | Campbell ........... C07C 2/68 585/456 |
| 8,569,561 | B2 | 10/2013 | Liu et al. |
| 8,692,048 | B2 | 4/2014 | Liu et al. |
| 8,921,636 | B2 * | 12/2014 | Cleverdon ......... C10G 29/205 422/187 |
| 9,079,175 | B1 | 7/2015 | Smith et al. |
| 9,079,176 | B1 | 7/2015 | Smith et al. |
| 9,120,092 | B1 | 9/2015 | Broderick et al. |
| 9,221,043 | B2 | 12/2015 | Broderick et al. |
| 2004/0133056 | A1 | 7/2004 | Liu et al. |
| 2007/0142690 | A1 | 6/2007 | Elomari |
| 2007/0249485 | A1* | 10/2007 | Elomari ............. B01J 31/0284 502/20 |
| 2009/0171134 | A1 | 7/2009 | Luo et al. |
| 2012/0172646 | A1 | 7/2012 | Liu et al. |
| 2012/0237410 | A1 | 9/2012 | Blais et al. |
| 2013/0066130 | A1 | 3/2013 | Luo et al. |
| 2013/0066132 | A1 | 3/2013 | Cleverdon et al. |

FOREIGN PATENT DOCUMENTS

| | | |
|---|---|---|
| CN | 103781746 A | 5/2014 |
| DE | 102009002600 A1 | 11/2009 |
| RU | 2303024 C2 | 8/2005 |
| WO | 2005042151 A1 | 5/2005 |
| WO | 2007073439 A1 | 6/2007 |
| WO | 2009085446 A1 | 7/2009 |
| WO | 2011015662 A2 | 2/2011 |
| WO | 2013039567 A1 | 3/2013 |
| WO | 2013061336 A2 | 5/2013 |

OTHER PUBLICATIONS

Search Report and Written Opinion for corresponding EP application No. 16828396.8, dated Nov. 30, 2018.
European Examination Report for corresponding European application No. 16 828 396.8-1101 dated Dec. 13, 2019.

* cited by examiner

MODIFIED HF ALKYLATION REACTION ZONE FOR IONIC LIQUID ALKYLATION

CROSS-REFERENCE TO RELATED APPLICATIONS

This application is a Continuation of International Application No. PCT/US2016/042888 filed Jul. 19, 2016 which application claims benefit of U.S. Provisional Application No. 62/196,171 filed Jul. 23, 2015, the contents of which cited applications are hereby incorporated by reference in their entirety.

BACKGROUND OF THE INVENTION

There are a variety of hydrocarbon conversion processes, and these processes utilize different catalysts.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.).

The alkylation of paraffins with olefins for the production of alkylate for gasoline can use a variety of catalysts. The choice of catalyst depends on the end product a producer desires. Typical alkylation catalysts include concentrated sulfuric acid or hydrofluoric acid. However, sulfuric acid and hydrofluoric acid are hazardous and corrosive, and their use in industrial processes requires a variety of environmental controls.

Ionic liquids provide advantages over other catalysts, including being less corrosive than catalysts like HF, and being non-volatile.

However, the current design for alkylation unit employing ionic liquid catalysts utilizes multiple mixer-reactors which increases capital expenses. The costs associated with the equipment needed to operate such a unit reduces the likelihood of commercial adoption of the process.

Therefore, there is a need a lower cost process for ionic liquid catalyzed alkylation.

SUMMARY OF THE INVENTION

One aspect of the present invention is an alkylation process. In one embodiment, the alkylation process includes pre-mixing a paraffin stream with an ionic liquid catalyst stream from a settler to form a pre-mixed paraffin and ionic liquid catalyst stream. The premixed paraffin and ionic liquid catalyst stream is mixed in a variable speed, low-efficiency pump to form a paraffin and ionic liquid catalyst mixture. An olefin feed stream is introduced into a riser reactor. The paraffin and ionic liquid catalyst mixture is introduced into the riser reactor to form a reaction mixture comprising alkylate and the ionic liquid catalyst. The reaction mixture is separated in a settler into an ionic liquid catalyst stream and a hydrocarbon stream.

Another aspect of the invention is an alkylation apparatus. In one embodiment, the alkylation apparatus includes a riser reactor having at least one inlet and an outlet; a settler having an inlet, a hydrocarbon outlet, and an ionic liquid outlet, the settler inlet being in fluid communication with the riser reactor outlet; a premixer having at least one inlet, and an outlet, the at least one inlet of the pre-mixer being in fluid communication with the ionic liquid outlet of the settler; and a variable speed, low efficiency pump having an inlet and an outlet, the pump inlet being in fluid communication with the premixer outlet, the pump outlet being in fluid communication with the at least one inlet of the riser reactor.

DETAILED DESCRIPTION OF THE INVENTION

The process closely follows current HF alkylation gravity feed reactor systems with some modifications, allowing the simple conversion of existing HF alkylation units to ionic liquid catalyst.

Figure 1:
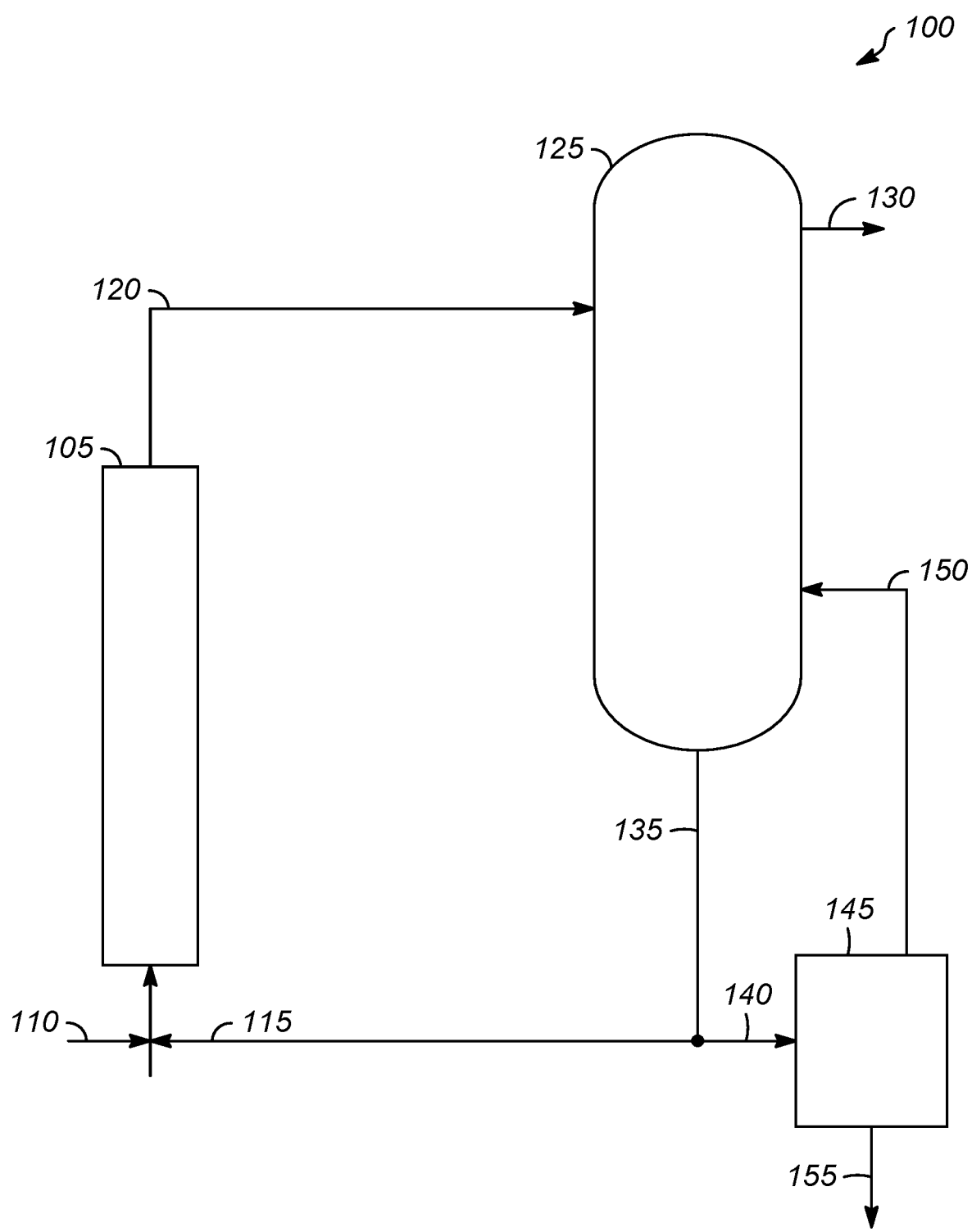
FIG. 1 illustrates one embodiment of an HF alkylation process.

FIG. 1 illustrates a typical HF alkylation unit 100. A riser reactor 105 receives a feed 110 and an HF alkylation catalyst 115.

The riser reactor 105 can provide the reaction effluent 120 to a settler 125. Several phases can form in the settler 125 including a hydrocarbon phase that can be extracted as a hydrocarbon effluent 130 and an acid phase 135. The riser reactor 105 and settler 125 can be operated at any suitable condition. Particularly, the riser reactor 105 can be operated at a pressure of about 440-about 800 kPa and the settler 125 can be operated at a pressure of no more than about 1,500 kPa, typically no more than about 1,100 kPa.

Generally, the hydrocarbon effluent 130 is provided to one or more columns (not shown) for separating out an alkylate product as well as recycling a paraffin, such as isobutane.

The acid phase 135 contains HF alkylation catalyst as well as some unreacted paraffin. The acid phase 135 can be at least partially spent and a portion can be recycled to the riser reactor 105 as HF alkylation catalyst 115 while another portion 140 is sent for regeneration in HF catalyst regeneration zone 145.

Exemplary settlers, alkylation reactors, and fractionation zones, are disclosed in, e.g., U.S. Pat. No. 5,098,668.

The HF catalyst regeneration zone 145 separates the HF catalyst and unreacted paraffin 150 from the acid soluble oils 155 formed during the alkylation process. The HF catalyst and unreacted paraffin 150 is sent to the settler 125, and the acid soluble oils 155 are removed. One example of an HF catalyst regeneration zone 145 is described in U.S. Pat. No. 8,227,366.

Figure 2:
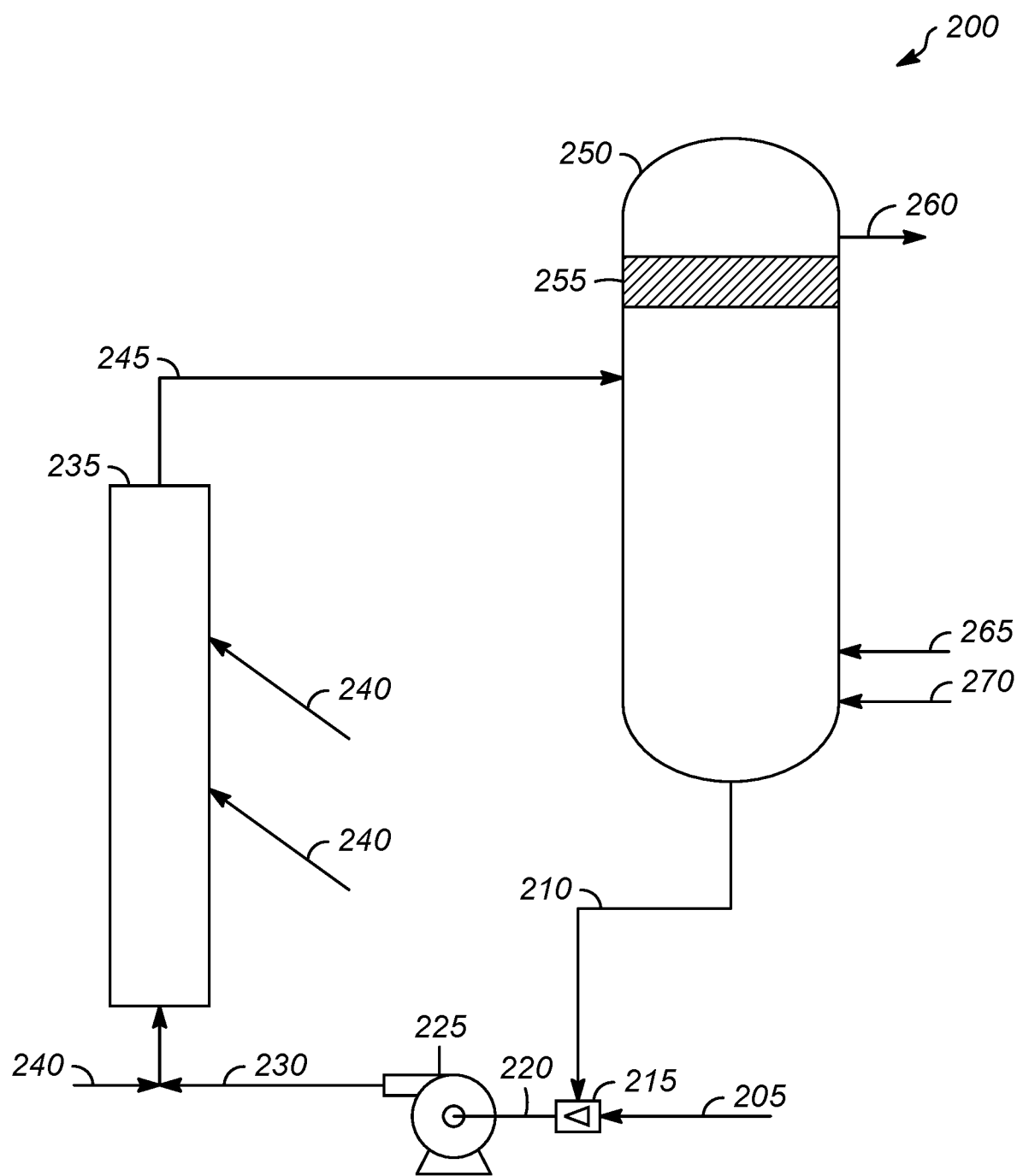
FIG. 2 illustrates one embodiment of an alkylation process according to the present invention.

This system can be easily modified to accommodate an ionic liquid catalyst. FIG. 2 shows an illustration of the process 200. The riser reactor and settler from the existing HF alkylation unit are maintained.

The paraffin stream 205 can include recycled paraffin from a downstream fractionation zone (not shown) and/or paraffin from one or more other refinery or chemical manufacturing units.

In some embodiments, the paraffin stream 205 is cooled to limit reactor outlet temperature. The paraffin stream 205 is pre-mixed with the ionic liquid catalyst stream 210 collected from the settler sump in a pre-mixer 215. The pre-mixer 215 could be a fixed or static mechanical mixer. For example, it could be a perforated pipe, a helical inline mixer, or a static mixer.

The premixed ionic liquid and paraffin stream 220 is processed through a low efficiency pump 225 which serves as a final mixer. A low efficiency pump utilizes a significant portion of the energy to produce droplets of one, some, or all of the fluids being moved through the pump, and to mix the fluids within the pump. In some embodiments, the low efficiency pump creates an emulsion of the ionic liquid in the paraffin. The term mixture is intended to cover emulsions. The low efficiency pump 225 can be a variable RPM mixer or a variable speed mixer to control the ionic liquid catalyst droplet size and size distribution. Suitable low efficiency pumps include, but are not limited to high shear pumps, rotor-stator pumps, and cavitation reactor pumps.

The paraffin and ionic liquid mixture stream 230 is sent to the reactor riser 235, along with an olefin feed stream 240. The olefin feed stream 240 could contain a single olefin, or a mixture of olefins. The olefin feed stream 240 could also contain any make-up paraffin needed. In some embodiments, the olefin feed stream 240 could be introduced at multiple elevations to help control residence time and to minimize the likelihood of localized spots of high olefin concentration. In some embodiments, the mixed olefin feed stream 240 is cooled to control the reactor outlet temperature.

Typical alkylation reaction conditions include a temperature in the range of about −20° C. to the decomposition temperature of the ionic liquid, or about −20° C. to about 100° C., or about −20° C. to about 80° C., or about 0° C. to about 80° C., or about 20° C. to about 80° C. It is preferred to have an ionic liquid that maintains its liquid state through the operating temperature range.

The pressure is typically in the range of atmospheric (0.1 MPa(g)) to about 8.0 MPa(g), or about 0.3 MPa(g) to about 2.5 MPa(g). The pressure is preferably sufficient to keep the reactants in the liquid phase.

The residence time of the reactants in the reaction zone is in the range of a few seconds to about 20 minutes, or about 30 sec to about 10 min, or about 1 min to 10 min, or about 1 min to 8 min, or about 1 min to 6 min, or about 2 min to 6 min.

Generally, the alkylation reaction is carried out with substantial molar excess of paraffin:olefin, typically in excess of about 0.5:1, usually about 1:1 to about 70:1, or about 1:1 to about 20:1. Usually, the system has a catalyst volume in the reactor of from about 1 vol % to about 50 vol %, or about 1 vol % to about 40 vol %, or about 1 vol % to about 30 vol %, or about 1 vol % to about 20 vol %, or about 1 vol % to about 10 vol %, or about 5 vol % to about 10 vol %.

The reactor riser effluent stream 245, which contains the alkylation products, the ionic liquid catalyst, and any unreacted paraffin, is sent to the vertical settler vessel 250 where the riser reactor effluent stream 245 separates into and ionic liquid catalyst phase and a hydrocarbon phase. Small amounts of the hydrocarbon may remain in the ionic liquid phase, and small amounts of ionic liquid may remain in the hydrocarbon phase (e.g., less than about 5%). The heavier ionic liquid phase accumulates in the sump.

In some embodiments, mechanical and/or non-mechanical separators 255, for example, a coalescing material, or contacting trays, are installed to prevent smaller drops of ionic liquid from being conveyed overhead with the hydrocarbon effluent 260. The hydrocarbon effluent 260 could be pressurized or pumped to the fractionation section (not shown). In some embodiments, a slipstream of paraffin 265 may be introduced into the bottom of the settler 250 via a sparger to prevent the ionic liquid catalyst from settling and solidifying. In some embodiments, a slipstream 270 may also be introduced into the bottom of the settler 250.

Multiple pre-mixers, low efficiency pumps, and/or risers could be provided to assist in residence time control and/or to increase throughput.

The paraffin used in the alkylation process preferably comprises a paraffin having from 2 to 10 carbon atoms, or 2 to 8 carbon atoms, or 4 to 8 carbon atoms, or 4 to 5 carbon atoms. In some embodiments, the paraffin is an isoparaffin having 3 to 10 carbons atoms, or 4 to 8 carbon atoms, or 4 to 5 carbon atoms. The olefin used in the alkylation process preferably has from 2 to 10 carbon atoms, or 2 to 8 carbon atoms, 3 to 8 carbon atoms, or 3 to 5 carbon atoms. One application of the process is to upgrade low value $C_3$-$C_5$ hydrocarbons to higher value alkylates.

Usually, the alkylation reaction can include the reaction of an isoparaffin, such as isobutane, with an olefin or other alkylating agent such as propylene, isobutylene, butene-1, butenes-2, and amylenes. Generally, the reaction of an isoparaffin with a $C_3$ or a $C_4$ olefin, such as isobutylene, butene-1, and/or butenes-2, is an example of a preferred reaction involving these specified materials and mixture.

One specific embodiment is the alkylation of butanes with butylenes to generate $C_8$ compounds. Preferred products include trimethylpentane (TMP), and while other $C_8$ isomers are produced, one competing isomer is dimethylhexane (DMH). The quality of the product stream can be measured in the ratio of TMP to DMH, with a high ratio desired.

The ionic liquid can be any acidic ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

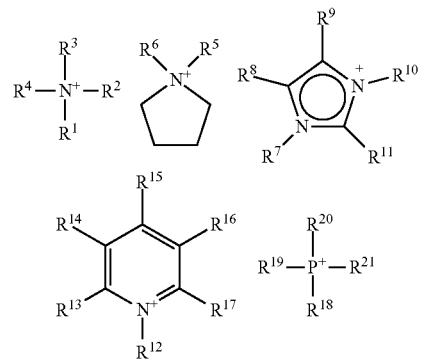

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

The anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from 0<Al <0.25 in the anion. Suitable anions include, but are not limited to, $AlC_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10^-}$, $GaCl_4^-$, $Ga_2C_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF4^-$.

A variety of methods for regenerating ionic liquids have been developed. For example, U.S. Pat. Nos. 7,651,970; 7,825,055; 7,956,002; 7,732,363, each of which is incorporated herein by reference, describe contacting ionic liquid containing the conjunct polymer with a reducing metal (e.g., Al), an inert hydrocarbon (e.g., hexane), and hydrogen and heating to about 100° C. to transfer the conjunct polymer to the hydrocarbon phase, allowing for the conjunct polymer to be removed from the ionic liquid phase. Another method involves contacting ionic liquid containing conjunct polymer with a reducing metal (e.g., Al) in the presence of an inert hydrocarbon (e.g. hexane) and heating to about 100° C. to transfer the conjunct polymer to the hydrocarbon phase, allowing for the conjunct polymer to be removed from the ionic liquid phase. See e.g., U.S. Pat. No. 7,674,739 B2; which is incorporated herein by reference. Still another method of regenerating the ionic liquid involves contacting the ionic liquid containing the conjunct polymer with a reducing metal (e.g., Al), HCl, and an inert hydrocarbon (e.g. hexane), and heating to about 100° C. to transfer the conjunct polymer to the hydrocarbon phase. See e.g., U.S. Pat. No. 7,727,925, which is incorporated herein by reference. The ionic liquid can be regenerated by adding a homogeneous metal hydrogenation catalyst (e.g., $(PPh_3)_3RhCl$) to ionic liquid containing conjunct polymer and an inert hydrocarbon (e.g. hexane), and introducing hydrogen. The conjunct polymer is reduced and transferred to the hydrocarbon layer. See e.g., U.S. Pat. No. 7,678,727, which is incorporated herein by reference. Another method for regenerating the ionic liquid involves adding HCl, isobutane, and an inert hydrocarbon to the ionic liquid containing the conjunct polymer and heating to about 100° C. The conjunct polymer reacts to form an uncharged complex, which transfers to the hydrocarbon phase. See e.g., U.S. Pat. No. 7,674,740, which is incorporated herein by reference. The ionic liquid could also be regenerated by adding a supported metal hydrogenation catalyst (e.g. Pd/C) to the ionic liquid containing the conjunct polymer and an inert hydrocarbon (e.g. hexane). Hydrogen is introduced and the conjunct polymer is reduced and transferred to the hydrocarbon layer. See e.g., U.S. Pat. No. 7,691,771, which is incorporated herein by reference. Still another method involves adding a suitable substrate (e.g. pyridine) to the ionic liquid containing the conjunct polymer. After a period of time, an inert hydrocarbon is added to wash away the liberated conjunct polymer. The ionic liquid precursor [butylpyridinium][Cl] is added to the ionic liquid (e.g. [butylpyridinium][$Al_2Cl_7$]) containing the conjunct polymer followed by an inert hydrocarbon.

After mixing, the hydrocarbon layer is separated, resulting in a regenerated ionic liquid. See, e.g., U.S. Pat. No. 7,737,067, which is incorporated herein by reference. Another method involves adding ionic liquid containing conjunct polymer to a suitable substrate (e.g. pyridine) and an electrochemical cell containing two aluminum electrodes and an inert hydrocarbon. A voltage is applied, and the current measured to determine the extent of reduction. After a given time, the inert hydrocarbon is separated, resulting in a regenerated ionic liquid. See, e.g., U.S. Pat. No. 8,524,623, which is incorporated herein by reference. Ionic liquids can also be regenerated by contacting with silane compounds (U.S. application Ser. No. 14/269,943), borane compounds (U.S. application Ser. No. 14/269,978), Bronsted acids, (U.S. application Ser. No. 14/229,329), or $C_1$ to $C_{10}$ Paraffins (U.S. application Ser. No. 14/229,403), each of which is incorporated herein by reference.

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a process comprising pre-mixing a paraffin stream with an ionic liquid catalyst stream from a settler to form a pre-mixed paraffin and ionic liquid catalyst stream; mixing the premixed paraffin and ionic liquid catalyst stream in a low efficiency pump to form a paraffin and ionic liquid catalyst mixture; introducing an olefin feed stream into a riser reactor; introducing the paraffin and ionic liquid catalyst mixture into the riser reactor to form a reaction mixture comprising alkylate and the ionic liquid catalyst; separating the reaction mixture in a settler into an ionic liquid catalyst stream and a hydrocarbon stream. An embodiment of the invention is one, any or all of prior embodiments in this paragraph up through the first embodiment in this paragraph wherein the hydrocarbon stream includes unreacted paraffin, and further comprising separating the hydrocarbon stream into an alkylate product stream and an paraffin recycle stream; wherein the paraffin recycle stream comprises at least a portion of the paraffin stream. An embodiment of the invention is one, any or all of prior embodiments in this paragraph up through the first embodiment in this paragraph further comprising cooling the paraffin stream. An embodiment of the invention is one, any or all of prior embodiments in this paragraph up through the first embodiment in this paragraph further comprising cooling the olefin feed stream. An embodiment of the invention is one, any or all of prior embodiments in this paragraph up through the first embodiment in this paragraph wherein introducing the olefin feed stream into the riser reactor comprises introducing the olefin feed stream into the riser reactor at more than one location. An embodiment of the invention is one, any or all of prior embodiments in this paragraph up through the first embodiment in this paragraph wherein the paraffin stream comprises an isoparaffin having from 3 to 10 carbon atoms. An embodiment of the invention is one, any or all of prior embodiments in this paragraph up through the first embodiment in this paragraph wherein the olefin feed stream comprises an olefin having from 2 to 10 carbon atoms. An embodiment of the invention is one, any or all of prior embodiments in this paragraph up through the first embodiment in this paragraph further comprising regenerating a portion of the ionic liquid catalyst before pre-mixing the paraffin stream with the ionic liquid catalyst stream. An embodiment of the invention is one, any or all of prior embodiments in this paragraph up through the first embodiment in this paragraph wherein the settler further comprises a coalescing material. An embodiment of the invention is one, any or all of prior embodiments in this paragraph up through the first embodiment in this paragraph further comprising introducing a slipstream of at least one of the paraffin and the ionic liquid catalyst into the bottom of the settler. An embodiment of the invention is one, any or all of prior embodiments in this paragraph up through the first embodiment in this paragraph further comprising mixing the olefin feed stream with the paraffin and ionic liquid catalyst mixture before introducing the olefin feed stream into the riser reactor.

A second embodiment of the invention is a process comprising pre-mixing an isoparaffin stream with an ionic liquid catalyst stream from a settler to form a pre-mixed isoparaffin and ionic liquid catalyst stream, the isoparaffin stream comprising isoparaffins having from 2 to 10 carbon atoms; mixing the premixed isoparaffin and ionic liquid catalyst stream in a low efficiency pump to form an isoparaffin and ionic liquid catalyst mixture; introducing an olefin feed stream to a riser reactor, the olefin feed stream comprising olefins having from 2 to 10 carbon atoms; introducing the isoparaffin and ionic liquid catalyst mixture into the riser reactor to form a reaction mixture comprising alkylate, unreacted isoparaffin, and the ionic liquid catalyst; separating the reaction mixture in the settler into an ionic liquid catalyst stream and a hydrocarbon stream comprising the alkylate and the unreacted isoparaffin; and separating the hydrocarbon stream into an alkylate product stream and an isoparaffin recycle stream; wherein the isoparaffin recycle stream comprises at least a portion of the isoparaffin stream. An embodiment of the invention is one, any or all of prior embodiments in this paragraph up through the second embodiment in this paragraph further comprising cooling at least one of the isoparaffin stream, and the olefin feed stream. An embodiment of the invention is one, any or all of prior embodiments in this paragraph up through the second embodiment in this paragraph wherein introducing the olefin feed stream to the riser reactor comprises introducing the olefin feed stream to the riser reactor at more than one location. An embodiment of the invention is one, any or all of prior embodiments in this paragraph up through the second embodiment in this paragraph further comprising regenerating a portion of the ionic liquid catalyst before pre-mixing the isoparaffin stream with the ionic liquid catalyst stream. An embodiment of the invention is one, any or all of prior embodiments in this paragraph up through the second embodiment in this paragraph wherein the settler further comprises a coalescing material. An embodiment of the invention is one, any or all of prior embodiments in this paragraph up through the second embodiment in this paragraph further comprising introducing a slipstream of at least one of isoparaffin and the ionic liquid catalyst into the bottom of the settler. An embodiment of the invention is one, any or all of prior embodiments in this paragraph up through the second embodiment in this paragraph further comprising mixing the olefin feed stream with the isoparaffin and ionic liquid catalyst mixture before introducing the olefin feed stream to the riser reactor.

A third embodiment of the invention is an apparatus comprising a riser reactor having at least one inlet and an outlet; a settler having an inlet, a hydrocarbon outlet, and an ionic liquid outlet, the settler inlet being in fluid communication with the riser reactor outlet; a premixer having at least one inlet, and an outlet, the at least one inlet of the pre-mixer being in fluid communication with the ionic liquid outlet of the settler; a low efficiency pump having an inlet and an outlet, the pump inlet being in fluid communication with the premixer outlet, the pump outlet being in fluid communication with the at least one inlet of the riser reactor. An embodiment of the invention is one, any or all of prior embodiments in this paragraph up through the third embodiment in this paragraph further comprising a fractionation zone having an inlet, a product outlet, and a paraffin outlet, the fractionation zone inlet being in fluid communication with the hydrocarbon outlet of the settler, the fractionation zone paraffin outlet being in fluid communication with the at least one inlet of the premixer.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. An ionic liquid alkylation process utilizing an existing HF alkylation unit, the existing HF alkylation unit comprising an existing settler and an existing riser reactor, the process comprising:
    modifying the existing HF alkylation unit by adding a pre-mixer and a low efficiency pump on a paraffin feed line, wherein the low efficiency pump comprises a high shear pump, a rotor-stator pump, or a cavitation reactor pump;
    pre-mixing a paraffin stream with an ionic liquid catalyst stream resulted from the existing settler in the pre-mixer to form a pre-mixed paraffin and ionic liquid catalyst stream;
    mixing the pre-mixed paraffin and ionic liquid catalyst stream in the low efficiency pump to form a paraffin and ionic liquid catalyst mixture, the low efficiency pump producing droplets of one or more of the paraffin or the ionic liquid catalyst in the paraffin and ionic liquid catalyst mixture;
    introducing an olefin feed stream into the existing riser reactor;
    introducing the paraffin and ionic liquid catalyst mixture into the existing riser reactor to form a reaction mixture comprising alkylate and the ionic liquid catalyst; and
    separating the reaction mixture in the existing settler into the ionic liquid catalyst stream and a hydrocarbon stream.

2. The process of claim 1 wherein the hydrocarbon stream includes unreacted paraffin, and the process further comprising:
    separating the hydrocarbon stream into alkylate product stream and a paraffin recycle stream;
    wherein the paraffin recycle stream comprises at least a portion of the paraffin stream.

3. The process of claim 1 further comprising:
    cooling at least one of the paraffin stream or the olefin feed stream from an initial temperature to a temperature less than the initial temperature.

4. The process of claim 1 wherein introducing the olefin feed stream into the existing riser reactor comprises introducing the olefin feed stream into the existing riser reactor at more than one location.

5. The process of claim 1 wherein the paraffin stream comprises an isoparaffin having from 4 to 10 carbon atoms.

6. The process of claim 1 wherein the olefin feed stream comprises an olefin having from 2 to 10 carbon atoms.

7. The process of claim 1 further comprising:
regenerating a portion of the ionic liquid catalyst stream before pre-mixing the paraffin stream with the ionic liquid catalyst stream.

8. The process of claim 1 wherein the existing settler further comprises a coalescing material.

9. The process of claim 1 further comprising introducing a slipstream of at least one of paraffin and ionic liquid catalyst into the bottom of the existing settler.

10. The process of claim 1 further comprising mixing the olefin feed stream with the paraffin and ionic liquid catalyst mixture before introducing the olefin feed stream into the existing riser reactor.

11. An ionic liquid alkylation process utilizing an existing HF alkylation unit, the existing HF alkylation unit comprising an existing settler and an existing riser reactor, the process comprising:
modifying the existing HF alkylation unit by adding a pre-mixer and a low efficiency pump on a paraffin feed line, wherein the low efficiency pump comprises a high shear pump, a rotor-stator pump, or a cavitation reactor pump;
pre-mixing an isoparaffin stream with an ionic liquid catalyst stream resulted from the existing settler in the pre-mixer to form a pre-mixed isoparaffin and ionic liquid catalyst stream, the isoparaffin stream comprising isoparaffins having from 4 to 10 carbon atoms;
mixing the pre-mixed isoparaffin and ionic liquid catalyst stream in the low efficiency pump to form an isoparaffin and ionic liquid catalyst mixture, the low efficiency pump producing droplets of one or more of the paraffin or the ionic liquid catalyst in the isoparaffin and ionic liquid catalyst mixture;
introducing an olefin feed stream to the existing riser reactor, the olefin feed stream comprising olefins having from 2 to 10 carbon atoms;
introducing the isoparaffin and ionic liquid catalyst mixture into the existing riser reactor to form a reaction mixture comprising alkylate, unreacted isoparaffin, and the ionic liquid catalyst;
introducing the reaction mixture into the existing settler;
separating the reaction mixture in the existing settler into the ionic liquid catalyst stream and a hydrocarbon stream comprising the alkylate and the unreacted isoparaffin; and
separating the hydrocarbon stream into an alkylate product stream and an isoparaffin recycle stream,
wherein the isoparaffin recycle stream comprises at least a portion of the isoparaffin stream.

12. The process of claim 11 further comprising:
cooling at least one of the isoparaffin stream or the olefin feed stream from an initial temperature to a temperature less than the initial temperature.

13. The process of claim 11 wherein introducing the olefin feed stream to the existing riser reactor comprises introducing the olefin feed stream to the existing riser reactor at more than one location.

14. The process of claim 11 further comprising:
regenerating a portion of the ionic liquid catalyst stream before pre-mixing the isoparaffin stream with the ionic liquid catalyst stream.

15. The process of claim 11 wherein the existing settler further comprises a coalescing material.

16. The process of claim 11 further comprising introducing a slipstream of isoparaffin, or a slipstream of ionic liquid catalyst, or a slipstream of isoparaffin and a slipstream of ionic liquid catalyst into the bottom of the existing settler, wherein the slipstream of isoparaffin, the slipstream of ionic liquid catalyst, and the slipstream of isoparaffin and the slipstream of ionic liquid catalyst are not the existing riser reactor effluent.

17. The process of claim 11 further comprising mixing the olefin feed stream with the isoparaffin and ionic liquid catalyst mixture before introducing the olefin feed stream to the existing riser reactor.

* * * * *